United States Patent [19]

Habicht et al.

[11] 4,323,688
[45] Apr. 6, 1982

[54] BENZIMIDAZOLE-2-CARBOXYLIC ACID AND DERIVATIVES THEREOF

[75] Inventors: Ernst Habicht, Oberwil; Pier G. Ferrini; Alfred Sallmann, both of Binningen, all of Switzerland

[73] Assignee: Ciba-Geigy Corporation, Ardsley, N.Y.

[21] Appl. No.: 928,632

[22] Filed: Jul. 27, 1978

[30] Foreign Application Priority Data

Aug. 1, 1977 [HU] Hungary .................... CI 1761
Feb. 27, 1978 [CH] Switzerland .................. 2094/78

[51] Int. Cl.³ .......................................... C07D 235/04
[52] U.S. Cl. ................................. 548/330; 548/331; 424/273 B
[58] Field of Search ............................. 548/331, 330

[56] References Cited

U.S. PATENT DOCUMENTS

| | | | |
|---|---|---|---|
| 2,053,822 | 9/1936 | Graenacher et al. | 548/330 |
| 2,876,233 | 3/1959 | Herrling et al. | 548/325 |
| 3,318,889 | 5/1967 | Bywater et al. | 548/330 |
| 3,325,271 | 6/1967 | Goldsmith et al. | 548/330 X |
| 3,661,925 | 5/1972 | McCally | 548/331 |
| 3,758,459 | 9/1973 | Fawvan et al. | 548/330 |
| 3,772,315 | 11/1973 | Regel et al. | 548/331 |

FOREIGN PATENT DOCUMENTS

| | | | |
|---|---|---|---|
| 574 | 7/1978 | European Pat. Off. | 548/331 |
| 7004376 | 10/1970 | Netherlands | 548/331 |
| 243766 | 7/1926 | United Kingdom | 548/330 |
| 766749 | 1/1957 | United Kingdom | |

OTHER PUBLICATIONS

Grantham et al., J. Chem. Soc. (c), 1969, pp. 70–74.
Garner et al., J. Chem. Soc. (c), 1967, pp. 2536–2540.
Chem. Abstracts 73:25359w.
Chem. Abstracts 37:4732⁷.

*Primary Examiner*—Ethel G. Love
*Attorney, Agent, or Firm*—Prabodh I. Almaula

[57] ABSTRACT

Novel substituted heterocyclyl compounds of the formula

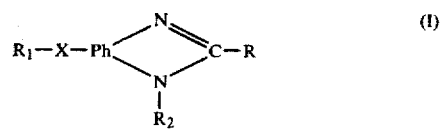

in which R is a free, esterified or amidated carboxyl group or a free, etherified or esterified hydroxymethyl group, $R_1$ is an aliphatic, cycloaliphatic, aromatic, araliphatic, heterocyclic or heterocyclic-aliphatic radical, $R_2$ is hydrogen or an aliphatic radical and Ph is a 1,2-phenylene group containing the radical $R_1$-X, and X is lower alkylidene or a direct bond, and pharmaceutically usable salts of compounds of the formula I with salt-forming properties as medicaments, pharmaceutical preparations containing these, their use as medicaments and also novel compounds of the formula I and salts of compounds of the formula I with salt-forming properties, with the proviso that $R_1$-X-Ph differs from 1,2-phenylene substituted by methyl in the 4- and/or 5-position when R is carboxyl, carbamyl or hydroxymethyl and $R_2$ is hydrogen, and pharmaceutically acceptable salts thereof are useful as anti-allergic agents.

5 Claims, No Drawings

BENZIMIDAZOLE-2-CARBOXYLIC ACID AND DERIVATIVES THEREOF

The invention relates to substituted heterocyclyl compounds, especially benz-substituted benzimidazole-2 derivatives of the formula

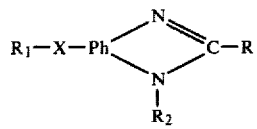

in which R is a free, esterified or amidated carboxyl group or a free, etherified or esterified hydroxymethyl group, $R_1$ is an aliphatic, cycloaliphatic, aromatic, araliphatic, heterocyclic or heterocyclic-aliphatic radical, $R_2$ is hydrogen or an aliphatic radical and Ph is a 1,2-phenylene group containing the radical $R_1$-X, and X is lower alkylidene or a direct bond, and pharmaceutically usable salts of compounds of the formula I with salt-forming properties as medicaments, pharmaceutical preparations containing these, their use as medicaments and also novel compounds of the formula I and salts of compounds of the formula I with salt-forming properties, with the proviso that $R_1$-X-Ph differs from 1,2-phenylene substituted by methyl in the 4- and/or 5-position when R is carboxyl, carbamyl or hydroxymethyl and $R_2$ is hydrogen, and processes for their preparation.

The invention relates, for example, to compounds of the formula I in which R, $R_1$, Ph and $R_2$ are as defined and either X is methylene, in which case $R_1$ has at least 2 carbon atoms when Ph is otherwise unsubstituted, $R_2$ is ethyl and R is acetoxymethyl, or X is a direct bond, in which case $R_1$ has at least 2 carbon atoms when Ph is otherwise unsubstituted, and $R_1$-X-Ph- differs from 1,2-phenylene substituted by methyl in the 4- and/or 5-position when R is carboxyl, carbamyl or hydroxymethyl and $R_2$ is hydrogen, and salts of such compounds with salt-forming properties, processes for their preparation, pharmaceutical preparations containing these and their use as medicaments.

In this specification the term "lower" used to qualify organic radicals and compounds denotes that these contain not more than 7, preferably not more than 4, carbon atoms.

In esterified carboxyl and etherified hydroxymethyl R, the etherified hydroxy group is, for example, a hydroxyl group etherified by an aliphatic or araliphatic radical, such as a substituted or unsubstituted aliphatic or araliphatic hydrocarbon radical, for example corresponding lower alkoxy or phenyl-lower alkoxy. Substituents of lower alkoxy are, inter alia, hydroxyl, lower alkoxy and/or di-lower alkylamino, and those of phenyl-lower alkoxy are, for example, lower alkyl, lower alkoxy and/or halogen, and one or more substituents can be present.

In amidated carboxyl, the amino group is, for example, unsubstituted amino or amino which is monosubstituted by hydroxyl, monosubstituted or disubstituted by lower alkyl or disubstituted by lower alkylene.

In esterified hydroxymethyl R, the esterified hydroxyl group is, for example, hydroxyl esterified by a carboxylic acid, such as an aliphatic or aromatic carboxylic acid, for example corresponding lower alkanoyloxy or benzoyloxy which is unsubstituted or substituted by lower alkyl, lower alkoxy and/or halogen. Lower alkanoyloxy is, for example, acetoxy, propionyloxy, butyryloxy, isobutyryloxy, valeroyloxy, caproyloxy or pivaloyloxy.

Aliphatic cycloaliphatic, aromatic and araliphatic radicals $R_1$ and $R_2$ are, in particular, substituted or unsubstituted aliphatic, cycloaliphatic, aromatic or araliphatic hydrocarbon radicals, such as corresponding lower alkyl, lower alkenyl, cycloalkyl, phenyl, naphthyl or phenyl-lower alkyl. Substituents are, for example, hydroxyl, lower alkoxy, lower alkylthio or phenylthio, lower alkanesulphinyl or benzenesulphinyl, or lower alkanesulphonyl or benzenesulphonyl, especially in the case of lower alkyl $R_1$ and lower alkyl $R_2$, and also lower alkyl, lower alkoxy and/or halogen, especially in the case of phenyl or phenyl-lower alkyl $R_1$. Heterocyclyl in a heterocyclic or heterocyclic-aliphatic radical $R_1$ is in particular monocyclic heterocyclyl of aromatic character containing one hetero-atom, such as oxygen, sulphur or nitrogen, as a ring member, such as furyl, thienyl or pyridyl. In a heterocyclic-aliphatic radical $R_1$, the aliphatic moiety is, for example, a corresponding aliphatic hydrocarbon radical, especially lower alkyl.

Lower alkylidene X is, for example, methylene.

Apart from being substituted by the radical $R_1$-X-, 1,2-phenylene can additionally be monosubstituted or polysubstituted, inter alia by lower alkyl, lower alkoxy, hydroxyl and/or halogen.

Lower alkoxy is, for example, methoxy, ethoxy, n-propoxy, isopropoxy, n-butoxy, isobutoxy, tert.-butoxy, n-pentyloxy or n-hexyloxy.

Phenyl-lower alkoxy is, for example, benzyloxy or 1- or 2-phenylethoxy.

Hydroxy-, lower alkoxy- and di-lower alkylamino-lower alkoxy is, in particular, 2- and/or 3-hydroxy-lower alkoxy, for example 2-hydroxyethoxy, 3-hydroxypropoxy or 2,3-dihydroxy-propoxy, and also 2- or 3-lower alkoxy-lower alkoxy, for example 2-methoxyethoxy, 2-ethoxyethoxy or 3-methoxypropoxy, and, respectively, di-lower alkylamino-lower alkoxy, for example dimethylaminoethoxy or diethylaminoethoxy.

Lower alkyl is, for example, methyl, ethyl, n-propyl, isopropyl, n-butyl, isobutyl, tert.-butyl, n-pentyl, n-hexyl or n-heptyl.

Halogen is in particular halogen with an atomic number of not more than 35, i.e. fluorine, chlorine or bromine.

Lower alkylene is, for example, 1,4-butylene, 1,5-pentylene or 1,6-hexylene.

Lower alkenyl is, for example, vinyl, 1-methyl-vinyl, 1-ethyl-vinyl, allyl, 2- or 3-methyl-allyl or 3,3-dimethyl-allyl.

Cycloalkyl preferably contains 3 to 8 ring atoms and is, for example, cyclopropyl, cyclopentyl, cyclohexyl, cycloheptyl or cyclooctyl.

Lower alkylthio is, for example, methylthio or ethylthio, whilst lower alkylsulphinyl and lower alkylsulphonyl are, for example, methylsulphinyl, ethylsulphinyl, methylsulphonyl or ethylsulphonyl.

Lower alkyl substituted by lower alkylthio, lower alkanesulphinyl or lower alkanesulphonyl is, for example, methylthio- or ethylthio-methyl, 1- or 2-methylthio- or 1- or 2-ethylthio-ethyl, or 2- or 3-methylthio- or 2- or 3-ethylthio-propyl, methanesulphinyl- or ethanesulphinyl-methyl, 1- or 2-methanesulphonyl- or 1- or 2-ethanesulphonyl-ethyl, or 2- or 3-methanesulphonyl- or 2- or 3-ethanesulphonyl-propyl. Lower alkyl substituted by phenylthio, benzenesulphinyl or benzenesulphonyl is, for example, phenylthio-, benzenesulphinyl- or benzenesulphonyl-methyl, or 1- or 2-phenylthio-, 1- or 2-benzenesulphinyl- or 1- or 2-benzenesulphonyl-ethyl.

Phenyl-lower alkyl is, for example, benzyl, 1- or 2-phenylethyl or 1-, 2- or 3-phenylpropyl.

Furyl is, for example, 2-furyl, and thienyl is, for example, 2-thienyl, whilst pyridyl can be 2-, 3- or 4-pyridyl.

Furyl-lower alkyl, thienyl-lower alkyl and pyridyl-lower alkyl are, in particular, correspondingly substituted methyl radicals, such as furfuryl, 2-thenyl or picolyl, for example 2- or 4-pyridylmethyl.

Salts are, for example, those of compounds of the formula I in which R is carboxyl, with bases. Such salts are, in particular, pharmaceutically usable, nontoxic salts, such as alkali metal salts or alkaline earth metal salts, for example sodium salts, potassium salts, magnesium salts or calcium salts, and also ammonium salts with ammonia or amines, such as lower alkylamines, for example trimethylamine or triethylamine, or mineral acid salts of compounds of formula I having a basic side chain, for example corresponding hydrohalides, such as hydrochlorides.

The novel compounds show valuable pharmacological properties. In particular, they show anti-allergic actions, which can be demonstrated, for example, on rats in doses of about 10 to about 100 mg/kg on oral administration in the passive cutaneous anaphylaxis test (PCA reaction), which is carried out analogously to the method described by Goose and Blair, Immunology, Volume 16, page 749 (1969), passive cutaneous anaphylaxis being produced by the procedure described by Ovary, Prog. Allergy, Volume 5, page 459 (1958). The anti-allergic action, especially the degranulation-inhibitory action, can also be determined in an in vitro experiment with the aid of the release of histamine from peritoneal cells of rats in the case of immunologically induced release (in which case, for example, rats infested with Nippostrongylus brasiliensis are used) and in the case of chemically induced release (in which case this is effected, for example, with a polymer of N-4-methoxyphenyl-ethyl-N-methyl-amine). The compounds of the present invention are useful as inhibitors of allergic reactions, for example in the treatment and prophylaxis of allergic diseases, such as asthma, including both extrinsic and intrinsic asthma, or other allergic diseases, such as allergic rhinitis, for example hay fever, conjunctivitis, or allergic dermatitis, for example urticaria or eczema.

The invention relates especially to compounds of the formula I in which R is free carboxyl or hydroxymethyl, esterified carboxyl or etherified hydroxymethyl containing, as the etherified hydroxyl group, lower alkoxy, hydroxy-lower alkoxy, lower alkoxy-lower alkoxy or di-lower alkylamino-lower alkoxy, amidated carboxyl containing, as the amino group, amino, hydroxyamino, lower alkylamino, di-lower alkylamino or lower alkyleneamino, or esterified hydroxymethyl containing, as the esterified hydroxyl group, lower alkanoyloxy or benzoyloxy which is unsubstituted or substituted by lower alkyl, lower alkoxy and/or halogen, $R_1$ is lower alkyl which is unsubstituted or substituted by lower alkoxy, lower alkylthio, lower alkanesulphinyl, lower alkanesulphonyl, phenylthio, benzenesulphinyl or benzenesulphonyl, or lower alkenyl, cycloalkyl, phenyl or phenyl-lower alkyl which are unsubstituted or substituted in the phenyl moiety by lower alkyl, lower alkoxy or halogen, or furyl, thienyl or pyridyl, or furyl-lower alkyl, thienyl-lower alkyl or pyridyl-lower alkyl, X is methylene, $R_2$ is hydrogen or lower alkyl and Ph is 1,2-phenylene which contains the radical $R_1$-X- and can be substituted by lower alkyl, lower alkoxy, hydroxyl and/or halogen, for example those in which $R_1$ contains at least 2 carbon atoms when Ph is otherwise unsubstituted, $R_2$ is ethyl and R is acetoxymethyl, and pharmaceutically usable salts of the said compounds in which R is carboxyl, processes for their preparation, pharmaceutical preparations containing these compounds and their use as medicaments.

The invention relates especially to compounds of the formula I, in which R is free carboxyl, esterified carboxyl containing, as the etherified hydroxyl group, lower alkoxy or hydroxy-lower alkoxy having not more than 4 carbon atoms, for example methoxy, ethoxy, 2-hydroxyethoxy, or 2,3-dihydroxypropoxy, or amidated carboxyl containing, as the amino group, amino or hydroxyamino, lower alkylamino or di-lower alkylamino, in which lower alkyl contains not more than 4 carbon atoms, for example methylamino, ethylamino, dimethylamino or diethylamino, or hydroxymethyl, etherified hydroxymethyl containing, as the etherified hydroxyl group, lower alkoxy having not more than 4 carbon atoms, for example methoxy or ethoxy, or di-lower alkylamino-lower alkoxy having not more than 4 carbon atoms in each alkyl moiety and in the alkoxy moiety, such as dimethylaminoethoxy, or esterified hydroxymethyl containing, as the esterified hydroxyl group, lower alkanoyloxy having not more than 7 carbon atoms, for example acetoxy, propionyloxy or pivaloyloxy, or benzoyloxy which is unsubstituted or substituted by lower alkyl, for example methyl, lower alkoxy, for example methoxy, and/or halogen, for example chlorine, $R_1$ is lower alkyl having not more than 7 carbon atoms, for example methyl, ethyl, n-propyl, isopropyl, n-butyl, isobutyl, tert.-butyl, n-pentyl, neopentyl, n-hexyl, or n-heptyl, lower alkoxy-, lower alkylthio-, lower alkanesulphinyl- or lower alkanesulphonyl-lower alkyl, in which the individual lower alkyl radicals contain not more than 4 carbon atoms, for example methoxy-, ethoxy-, methylthio-, ethylthio-, methanesulphinyl-, ethanesulphinyl-, methanesulphonyl- or ethanesulphonyl-methyl, 1- or 2-methoxy-, 1- or 2-ethoxy-, 1- or 2-methylthio-, 1- or 2-ethylthio-, 1- or 2-methanesulphinyl-, 1- or 2-ethanesulphinyl-, 1- or 2-methanesulphonyl- or 1- or 2-ethanesulphonyl-ethyl, or 1-, 2- or 3-methoxy-, 1-, 2- or 3-ethoxy-, 1-, 2- or 3-methylthio-, 1-, 2- or 3-ethylthio-, 1-, 2- or 3-methanesulphinyl-, 1-, 2- or 3-ethanesulphinyl-, 1-, 2- or 3-methanesulphonyl- or 1-, 2- or 3-ethanesulphonyl-propyl, phenylthio-, benzenesulphinyl- or benzenesulphonyl-lower alkyl, in which the lower alkyl radical contains not more than 4 carbon atoms, for example phenylthio-, benzenesulphinyl- or benzenesulphonyl-methyl, 1- or 2-phenylthio-, 1- or 2-benzenesulphinyl- or 1- or 2-benzenesulphonyl-ethyl, or 1-, 2- or 3-phenylthio-, 1-, 2- or 3-benzenesulphinyl- or 1-, 2- or 3-benzenesulphonyl-propyl, lower alkenyl having not more than 5 carbon atoms, for example 1-methyl- or 1-ethyl-vinyl or allyl, cycloalkyl having not more than 7 carbon atoms, for example cyclopropyl or cyclohexyl, phenyl or phenyl-lower alkyl having not more than 4 carbon atoms in the lower alkyl radical, for example benzyl or 1- or 2-phenylethyl, which are unsubstituted or substituted by lower alkyl having not more than 4 carbon atoms, for example methyl, lower alkoxy having not more than 4 carbon atoms, for example methoxy, and/or halogen with an atomic number of not more than 35, for example chlorine or bromine, or furyl, thienyl or pyridyl, for example 2-furyl, 2-thienyl or 2-, 3- or 4-pyridyl, or furyl-, thienyl- or pyridyl-lower alkyl having not more than 4 carbon atoms in the lower alkyl radical, for example furfuryl, 2-thenyl or 2- or 4-picolyl, X is methylene, $R_2$ is hydrogen or lower alkyl having not more than 4 carbon atoms, for example methyl, and Ph is 1,2-phenylene which contains the radical of the formula $R_1$-X- and can be substituted by lower alkyl having not more than 4 carbon atoms, for example methyl, lower alkoxy having not more than 4 carbon atoms, for example methoxy, hydroxyl and/or halogen with an atomic number of not more than 35, for example chlorine or bromine, the radical of the formula $R_1$-X- assuming any position suitable for substitution, preferably the 4-position or 5-position of the 1,2-phenylene radical, for example those compounds in which $R_1$ contains at least 2 carbon atoms when Ph is otherwise unsubstituted, $R_2$ is ethyl and R is acetoxymethyl, and pharmaceutically usable salts of the said compounds, in which R is carboxyl, with bases, processes for their preparation, pharmaceutical preparations containing these compounds and their use as medicaments.

The invention relates in particular to compounds of the formula

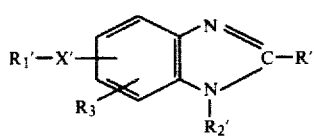

(Ia)

in which R' on the one hand is in particular carboxyl or also esterified carboxyl containing, as the etherified hydroxyl group, lower alkoxy having not more than 4 carbon atoms, for example methoxy or ethoxy, and on the other hand is in particular hydroxymethyl or also etherified hydroxymethyl containing, as the etherified hydroxyl group, lower alkoxy having not more than 4 carbon atoms, for example methoxy or ethoxy, and in which $R_1'$ is lower alkyl having not more than 7 carbon atoms, for example methyl, ethyl, n-propyl, n-butyl or tert.-butyl, cycloalkyl having not more than 6 carbon atoms, for example cyclopropyl or cyclohexyl, or phenyl, X' is methylene, $R_2'$ is hydrogen or lower alkyl having not more than 4 carbon atoms, for example methyl, and $R_3$ is hydrogen, lower alkyl having not more than 4 carbon atoms, for example methyl, lower alkoxy having not more than 4 carbon atoms, for example methoxy, or halogen with an atomic number of not more than 35, for example chlorine, the radical of the formula $R_1'$-X'- and the group $R_3$, if the latter differs from hydrogen, preferably assuming the 5-position and the 6-position of the benzimidazole ring, and pharmaceutically usable salts of compounds of the formula Ia, in which R' is carboxyl, with bases, as medicaments, pharmaceutical preparations containing these, their use as medicaments and also compounds of the formula Ia and pharmaceutically usable salts of compounds of the formula Ia, in which R' is carboxyl, with bases on their own and processes for their preparation.

The invention relates in particular to compounds of the formula Ia in which R' is carboxyl or esterified carboxyl containing, as the etherified hydroxyl group, lower alkoxy having not more than 4 carbon atoms, for example methoxy or ethoxy, and in which $R_1'$-X'- is lower alkyl having 2 to 7 carbon atoms, for example ethyl, n-propyl, isopropyl, n-butyl, n-pentyl or n-hexyl, cycloalkylmethyl having not more than 6 ring carbon atoms, for example cyclopropylmethyl or cyclohexylmethyl, or benzyl, $R_2'$ is hydrogen or especially lower alkyl having not more than 4 carbon atoms, for example methyl, and $R_3$ is hydrogen or lower alkyl having not more than 4 carbon atoms, for example methyl, lower alkoxy having not more than 4 carbon atoms, for example methoxy, or halogen with an atomic number of not more than 35, for example chlorine, the radicals $R_1'$-X- and $R_3$ preferably assuming the 5-position and, respectively, the 6-position of the benzimidazole ring, and pharmaceutically usable salts of compounds of the formula Ia, in which R' is carboxyl, with bases, as medicaments, pharmaceutical preparations containing these, their use as medicaments and also compounds of the formula Ia and pharmaceutically usable salts of these compounds with salt-forming properties, and processes for their preparation.

The invention relates very particularly to compounds of the formula Ia in which R' is carboxyl, hydroxymethyl or lower alkoxycarbonyl or lower alkoxymethyl having a total of not more than 5 carbon atoms, for example methoxy- or ethoxy-carbonyl or -methyl, $R_1'$-X' is lower alkyl having not more than 8, for example having not more than 5, carbon atoms, for example methyl, ethyl, n-propyl, isopropyl, n-butyl, isobutyl or n-pentyl, and $R_2'$ and $R_3$ independently of one another are hydrogen or lower alkyl having not more than 4 carbon atoms, such as methyl, and pharmaceutically usable salts of compounds of the formula Ia, in which R' is carboxyl, with bases, as medicaments, pharmaceutical preparations containing these, their use as medicaments and also compounds of the formula Ia and pharmaceutically usable salts of these compounds with salt-forming properties, in which R' is carboxyl, with bases on their own, with the proviso that a methyl group $R_1'$-X'- does not assume the 5(6)-position of the benzimidazole ring when $R_3$ is hydrogen or is methyl bonded in the 6(5)-position, $R_2'$ is hydrogen and R' is carboxyl or hydroxymethyl, and processes for their preparation.

The invention relates very particularly to, for example, compounds of the formula Ia in which R' is either carboxyl or lower alkoxycarbonyl having a total of not more than 5 carbon atoms, such as methoxy- or ethoxycarbonyl, and in which $R_1'$-X'- is lower alkyl having not more than 7 carbon atoms, for example methyl, ethyl, n-propyl, isopropyl, n-butyl, n-pentyl or n-hexyl, and $R_2'$ and $R_3$ are lower alkyl having not more than 4 carbon atoms, for example methyl, the radical $R_1'$-X'- assuming the 5-position of the benzimidazole ring and the lower alkyl radical $R_3$ assuming the 6-position of the benzimidazole ring, and salts of such compounds, in which R' is carboxyl, with bases, and also processes for their preparation, the said compounds and pharmaceutically usable salts of such compounds, in which R' is carboxyl, with bases, as medicaments, pharmaceutical preparations containing these and their use as medicaments.

The invention also relates very particularly to, for example, compounds of the formula Ia in which R' is carboxyl, $R_1'$ is lower alkyl having not more than 7, for example having not more than 4, carbon atoms, such as methyl, ethyl, n-propyl, isopropyl or n-butyl, X' is methylene, $R_2'$ is hydrogen and $R_3$ is hydrogen or lower alkyl having not more than 4 carbon atoms, such as methyl, the radical $R_1'$-$X'$- assuming the 5-position of the benzimidazole ring and a lower alkyl radical $R_3$ assuming the 6-position of the benzimidazole ring, and also processes for their preparation, the said compounds and pharmaceutically usable salts of such compounds, in which $R'$ is carboxyl, with bases, as medicaments, pharmaceutical preparations containing these and their use as medicaments.

The invention relates specifically to the compounds of the formula I named in the examples.

The novel compounds can be prepared in a manner known per se. Thus, for example, they can be obtained by cyclising a compound of the formula II

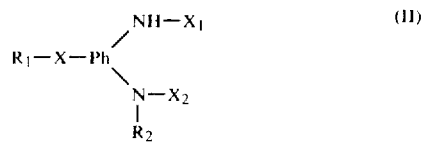

in which one of the radicals $X_1$ and $X_2$ is a group of the formula —C(=O)-R and the other is hydrogen, or a salt thereof, and, if desired, converting a compound thus obtainable into another compound of the formula I and/or converting a resulting free salt-forming compound into a salt or converting a resulting salt into the free compound or into another salt.

Salts of starting materials of the formula II are, for example, acid addition salts, such as hydrohalides, for example the hydrochlorides, of compounds in which R is free, etherified or esterified hydroxymethyl, and alkali metal salts or ammonium salts, for example the sodium salts, of compounds in which R is carboxyl.

The cyclisation is effected in a conventional manner, at normal or, especially for the preparation of compounds in which R is free or etherified hydroxymethyl, at elevated temperature, for example at about 50° C. to about 160° C., in particular at about 110° C. to 140° C., if necessary in the presence of an acid condensing agent, such as a hydrogen halide acid, for example hydrochloric acid, and/or of a water-binding agent, for example dicyclohexylcarbodiimide, and advantageously under an inert gas, for example under nitrogen.

The above process variant is especially suitable for the preparation of compounds of the formula I in which R is free or etherified hydroxymethyl, which compounds can subsequently easily be converted in a conventional manner into other compounds of the formula I.

The starting materials of the formula II are advantageously prepared in situ, for example by reacting a corresponding 1,2-phenylenediamine, which is substituted by the radical $R_1$-X- and can also contain yet further substituents, i.e. a compound of the formula

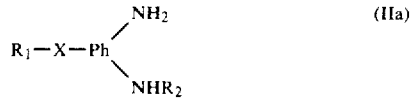

or an acid addition salt thereof, for example the hydrochloride thereof, with an acid of the formula R-COOH (IIb) or a suitable reactive derivative, preferably an ester, such as a lower alkyl ester, amide, anhydride, such as acid halide, imino-ether, such as imino-lower alkyl ether or imino-ester, such as imino-chloride, thereof, for example with glycollic acid, which is preferably etherified, or with ethyl chlorooxalate or bromooxalate, if necessary in the presence of a solvent or diluent, such as a lower alkanol, for example methanol or ethanol, and/or with warming to about 50° C. to about 160° C., for example to about 110° C. to about 140° C. The 1,2-phenylenediamines which are to be used as the starting materials for this reaction can be obtained by a conventional reduction of the corresponding 1,2-nitraniline compound, for example by reaction thereof with a chemical reducing agent, such as sodium dithionite, or with suitably activated hydrogen, such as hydrogen catalytically activated by a noble metal catalyst in a basic medium, for example by Raney nickel in methanol or ethanol. In a modification of this method, it is also possible to react this 1,2-nitraniline intermediate with the abovementioned acid, for example with glycollic acid or oxalic acid, or with a suitable derivative thereof, for example with a lower alkyl ethoxyacetate or chlorooxalate, and subsequently to reduce the nitro group, for example with hydrogen in the presence of Raney nickel.

If they are not known compounds, the 1,2-nitraniline compounds to be used for the preparation of the starting materials of the formula II can be prepared, for example, using corresponding chlorobenzenes of the formula H-PhH-Cl as the starting material, by substituting these compounds in a conventional manner, for example by reaction with a compound of the formula $R_1$-X-Hal or $R_1$-X-OH or with a corresponding alkene or cycloalkene in the presence of aluminium chloride, nitrating the compound of the formula $R_1$-X-PhH-Cl, thus obtainable, with nitric acid/sulphuric acid and reacting the chloronitro compound of the formula $R_1$-X-Ph(Cl)-$NO_2$, thus obtainable, with ammonia or an amine of the formula $R_2NH_2$.

A preferred embodiment of the process described above comprises reacting a compound of the formula

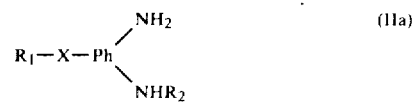

with an acid of the formula R-COOH (IIb) or a suitable functional derivative thereof and, if desired, converting a compound, thus obtainable, into another compound of the formula I and/or converting a resulting free salt-forming compound into a salt or converting a resulting salt into the free compound or into another salt.

Suitable functional derivatives of acids of the formula IIb are, for example, their esters, such as the lower alkyl esters, amides or anhydrides, such as acid halides. Acids of the formula IIb, and the functional derivatives thereof, to be employed in the above process variant are, for example, free or etherified glyoxylic acid and ethyl chlorooxalate or bromooxalate.

The reaction is carried out in particular in the presence of a solvent or diluent, such as of a lower alkanol, for example methanol or ethanol, if necessary with warming to about 50° C. to 160° C., for example to about 110° C. to about 140° C.

The novel compounds can also be prepared by converting $X_3$ in a compound of the formula

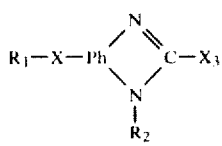
(III)

in which $X_3$ is a radical convertible to the group R, into the group R and, if desired, converting a compound of the formula I, thus obtainable, into another compound of the formula I and/or, if desired, converting a resulting salt into the free compound or into another salt and/or converting a free salt-forming compound into a salt.

A group $X_3$ is, in particular, a radical which can be converted by oxidation to the carboxyl group or by reduction to hydroxymethyl R and is especially the formyl group, and, in the course of the oxidation reaction, this group can also be formed in situ, for example from the methyl or aminomethyl group or from a hydroxymethyl group esterified by an inorganic acid, such as a hydrogen halide acid, for example by hydrochloric acid, or etherified by a cyclic 2-hydroxy-ether, for example by 2-hydroxytetrahydropyrane, or a cyclic 2- or 4-hydroxythioether, for example by 2-hydroxytetrahydrothiopyrane, 2-hydroxytetrahydrothiophene or 4-hydroxy-4-methoxy-tetrahydrothiopyrane, or set free from one of its derivatives, such as a lower alkylene acetal or di-lower alkyl acetal or imino, for example benzylimine or an imminium salt, such as a N,N-di-lower alkyl-imminium salt, for example a N,N-dimethylimminium salt, for example N,N-dimethylimminium chloride or N,N-dimethylimminium methosulphate. Furthermore, 2-furyl which is unsubstituted or substituted, for example which contains di-lower alkoxymethyl in the 5-position, can be converted by oxidation to the carboxyl group.

The oxidation can be carried out in a manner known per se, for example by treatment with an oxidising heavy metal compound, and in the case of starting materials of the formula II in which $X_3$ is the formyl group or a radical which is convertible to the latter by oxidation, such as one of the said esterified or etherified hydroxymethyl groups, or substituted or unsubstituted 2-furyl, preferably with an oxidising compound containing chromium-VI or manganese-VII, for example chromium trioxide or in particular potassium permanganate, and in the case of starting materials of the formula II in which $X_3$ is one of the said etherified hydroxymethyl groups also with an oxidising compound containing manganese-IV, such as manganese dioxide. The reaction is advantageously carried out in the presence of a suitable solvent or diluent, for example of acetone or pyridine, or of a mixture thereof, preferably an aqueous mixture thereof, if necessary with cooling or warming, for example in a temperature range from about 0° C. to about 80° C.

A formyl group can, for example, also be reduced to hydroxymethyl by reduction with a light metal hydride or di-(light metal) hydride, such as a boron hydride, sodium borohydride or lithium aluminium hydride, for example with sodium borohydride or with sodium cyanoborohydride in a lower alkanol, lithium aluminium hydride in ether or diisoamylborane in tetrahydrofuran, if necessary with cooling or gentle warming, for example at about 0° C. to about 100° C., and/or under an inert gas, such as nitrogen.

Further radicals $X_3$ which are convertible to the groups of the formula R are functionally modified carboxyl groups which differ from the free, esterified or amidated carboxyl group of the formula R and are convertible into the latter, such as cyano, halogenocarbonyl, for example chlorocarbonyl, reactive esterified carboxyl groups, such as mono-, di- or tri-halogeno-ethoxycarbonyl, for example chloro-, di-chloro- or tri-chloro-ethoxycarbonyl, phenoxy- or 4-nitrophenoxy- or 2,4-dinitrophenoxycarbonyl, or reactive carbamyl groups, such as imidazolyl-2-carbonyl, openchain or cyclic imino-ether groups, for example imino-lower alkyl ether groups or 4,4- or 5,5-dimethyl-4,5-dihydro-2-oxazolyl, or 4,4,6-trimethyl-5,6-dihydro-2-oxazinyl, or tri-lower alkoxy- or trihalogeno-methyl groups, for example trichloromethyl. These groups can be converted to the carboxyl group by solvolysis, for example hydrolysis, usually in the presence of an acid or preferably an alkaline hydrolysing agent, such as of an organic sulphonic acid, for example p-toluenesulphonic acid or mesitylenesulphonic acid, or of a mineral acid, for example sulphuric acid, or of an alkali metal hydroxide, for example sodium hydroxide, and a tri-lower alkoxymethyl or imino-ether group can also be converted to esterified carboxyl, or a cyano group $X_3$ can also be converted to the carbamyl group. The hydrolysis of cyano and trihalogenomethyl is preferably carried out under basic conditions and the hydrolysis of imino-ether groups is preferably carried out under acid conditions. The treatment of a starting material of the formula II in which $X_3$ is halogenocarbonyl or one of the said reactive esterified carboxyl groups with an alcohol, for example a lower alkanol, ammonia or a corresponding amine, if necessary in the presence of a basic agent, for example of pyridine, yields compounds of the formula I in which R is an esterified or amidated carboxyl group, for example lower alkoxycarbonyl. If a starting material of the formula II in which $X_3$ is trihalogenomethyl, especially trichloromethyl, is reacted with an alcohol, such as a lower alkanol, or with ammonia, hydroxylamine or a primary or secondary amine and then with water, a compound of the formula I in which R is esterified or amidated carboxyl can be formed direct. The said reactive esterified carboxyl groups and carbamyl groups can likewise be solvolysed to amidated carboxyl groups by reaction with ammonia or a corresponding amine. The above reactions can be carried out by methods known per se, usually in the presence of a solvent or diluent or of a mixture thereof and, if necessary, with cooling or warming, for example in a temperature range from about 0° C. to about 120° C.

Further radicals $X_3$ which are convertible to groups of the formula R by solvolysis are, for example, esterified or etherified hydroxymethyl groups which differ from free, esterified or etherified hydroxymethyl and are convertible to the latter by solvolysis. Such esterified hydroxymethyl groups are, for example, hydroxymethyl groups esterified by inorganic acids, such as hydrogen halide acids, for example chloromethyl or bromomethyl. Etherified hydroxymethyl groups of the type defined above are, for example, hydroxymethyl groups etherified by a cyclic, preferably 5-membered or 6-membered, 2- or 4-hydroxy-ether or -thioether, for example by 2-hydroxytetrahydropyrane, 2-hydroxytetrahydrothiopyrane, 2-hydroxytetrahydrothiophene or 4-hydroxy-4-methoxy-tetrahydrothiopyrane, or by a silanol, such as a tri-lower alkylsilanol, for example by trimethylsilanol. The said groups can be hyrolysed to hydroxymethyl in a conventional manner, for example in the presence of an acid or, in particular, a basic hydrolysing agent, such as of an organic sulphonic acid, for example of p-toluenesulphonic acid or mesitylenesulphonic acid, or of a mineral acid, for example of sulphuric acid or hydrochloric acid, or of an alkali metal hydroxide, for example of sodium hydroxide. The hydrolysis of esterified hydroxymethyl groups is preferably carried out under basic conditions, for example in sodium hydroxide solution. The hydrolysis of hydroxymethyl groups etherified by hydroxy-ethers or hydroxy-thioethers is preferably effected under mild acid conditions, for example by means of p-toluenesulphonic acid in methanol or toluene. Thioether compounds can also be hydrolysed under neutral conditions in the presence of silver salts, such as silver nitrate. No assistants are necessary for the hydrolysis of silanyloxymethyl groups. Hydroxymethyl groups esterified in the indicated manner can also be solvolysed to etherified hydroxymethyl groups R by reaction with a corresponding alcohol, such as a lower alkanol, or preferably a corresponding metal alcoholate, such as an alkali metal lower alkanolate, for example the sodium lower alkanolate.

The starting materials can be prepared in a manner known per se.

Starting materials of the formula II in which $X_3$ is a cyclic imino-ether group or a hydroxymethyl group etherified by a cyclic 2- or 4-hydroxy-ether or 2- or 4-hydroxy-thioether can be prepared, for example, by reacting a corresponding compound of the formula

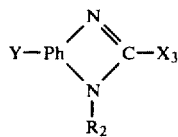

(IIIa)

in which Y is a group -M-Hal or -M/2, M is a metal atom of group II of the periodic table of the elements and Hal is chlorine, bromine or iodine, with a halide of the formula $R_1$-X-Hal and hydrolysing the primary product in a conventional manner. The compounds of the formula IIIa used as starting materials for this reaction are advantageously prepared in situ, by first converting the group $Y_1$ in a compound of the formula

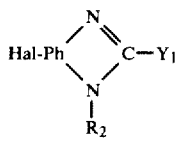

(IIIb)

in which Hal is chlorine, bromine or iodine and $Y_1$ is carboxyl, cyano or hydroxymethyl, to a radical $X_3$ and then converting Hal by reaction with the corresponding metal, for example with magnesium, to the group Y, for example of the formula -MgHal. Compounds of the formula IIIa in which Y differs from magnesium and is, for example, a group -Cd/2 can also be prepared by reaction of the corresponding halogenomagnesium compounds with a salt of the formula $MHal_2$, for example with cadmium chloride. The conversion of $Y_1$ to the said groups is effected in a conventional manner. Carboxyl can, for example, either first be converted to halogenocarbonyl, for example by means of thionyl chloride in methylene chloride, and then, by reaction with the particular aminoalkanol, for example with aminoisobutanol, or by reaction with the particular aziridine, for example with 2,2-dimethylaziridine, and subsequent acid-catalysed ring extension, to one of the said imino-ether groups, for example to 4,4- or 5,5-dimethyl-4,5-dihydro-2-oxazolyl. Cyano can likewise be converted to an imino-ether group, for example to 4,4,6-trimethyl-5,6-dihydro-2-oxazinyl, by reaction with the particular aminoalkanol or alkanediol, for example with 4-amino-2-methyl-pentan-2-ol or 2-methyl-pentane-2,4-diol, under acid catalysis. Hydroxymethyl can, for example, be etherified by reaction with a chlorosilane, for example with trimethylchlorosilane in pyridine, or converted to hydroxymethyl etherified by a cyclic 2- or 4-hydroxy-ether or -thioether, for example to 2-tetrahydropyranyloxymethyl, 2-tetrahydrothiopyranyloxymethyl, 2-tetrahydrothienyloxymethyl or 4-(4-methoxy)-tetrahydropyranyloxymethyl, using a corresponding unsaturated cyclic ether or thioether, for example using dihydropyrane, dihydrothiopyrane, 2,3-dihydrothiophene or 4-methoxy-1,2-dihydro-γ-thiopyrane, under acid catalysis, for example with p-toluenesulphonic acid in toluene or acetone. Analogously, compounds of the formula III in which $X_3$ is formyl can also be prepared by converting Hal in a compound of the formula IIIb in which $Y_1$ is acetalised formyl, such as lower alkylenedioxymethyl or di-lower alkoxymethyl, to a group Y and then to a group $R_1$-X-and hydrolysing the acetalised formyl group, for example under acid catalysis.

Other starting materials of the formula III can be prepared using, as starting materials, the corresponding 1,2-phenylenediamines which are substituted by the radical of the formula $R_1$-X- and can contain further substituents and which are accessible from the corresponding nitroanilino compounds by reduction of the nitro group, for example with hydrogen in the presence of Raney nickel, in a manner analogous to that described for the treatment of these compounds with glycollic acid or a suitable reactive derivative thereof, for example by reaction with an acid of the formula $X_3$-COOH, such as a mono- or trihalogenoacetic acid, di-lower alkoxyacetic acid or 5-di-lower alkoxymethylfuran-2-carboxylic acid, or a reactive derivative thereof, such as a lower alkyl ester thereof.

Furthermore, starting materials of the formula III in which $X_3$ is formyl or cyano can also be obtained by reacting a benzimidazole which is unsubstituted in the 1-position and 2-position, contains the group $R_1$-X- in the carbocyclic ring and can contain further substituents, with 2-chloro-1,1,2-trifluoro-ethene and reacting the 1-(2-chloro-1,1,2-trifluoroethyl)-benzimidazole which is thus obtainable and is unsubstituted in the 2-position and in the carbocyclic moiety contains the group $R_1$ and can contain further substituents, with an alcohol, such as a lower alkanol, for example ethanol, in the presence of a base, such as of an alkali metal hydroxide, for example sodium hydroxide, or with a hydroxylamine acid addition salt, for example the hydrochloride, in the presence of a base, for example pyridine. This yields a compound of the formula III in which $X_3$ is an acetalised formyl group, such as di-lower alkoxymethyl, for example diethoxymethyl, or the hydroximinomethyl group, which can be converted in a manner known per se, for example by hydrolysis to the formyl group $X_3$, or by dehydration, for example with phosphorus pentoxide or 4-methylphenylsulphonyl chloride, to the cyano group $X_3$.

A starting material of the formula III in which $X_3$ is cyano can also be obtained, for example, by treating a compound of the formula III in which $X_3$ is trihalogenomethyl, for example trichloromethyl, with aqueous ammonia.

The novel compounds can also be prepared by reacting a compound of the formula

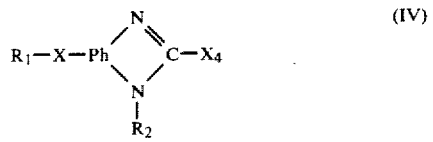

with a reactive derivative of carbonic acid, for example with carbon dioxide or a compound of the formula R-X$_5$ (V), in which formulae $X_4$ is a metal radical and $X_5$ is a halogen atom, and, if desired, converting a compound of the formula I, thus obtainable, into another compound of the formula I and/or, if desired, converting a resulting salt into the free compound or into another salt and/or converting a free salt-forming compound into a salt.

Metal radicals are, for example, groups of the formula -M$^I$, -M$^{II}$-Hal or -M$^{II}$/2, in which M$^I$ is a metal atom of group I and M$^{II}$ is a metal atom of group II of the periodic table of the elements and Hal is halogen, such as chlorine, bromine or iodine. Preferred metal radicals of the said type are those of the formulae -Li, -MgHal and -Cd/2.

Compounds of the formula V are, for example, corresponding halogenoformates, for example lower alkyl chloroformates. Halogen atoms are, for example, chlorine, bromine or iodine atoms.

The reaction of compounds of the formulae IV and V is carried out in a conventional manner, advantageously in an inert solvent, such as an ether, for example in diethyl ether or tetrahydrofuran, a hydrocarbon, for example benzene, or mixtures thereof, if necessary with cooling or gentle warming, for example at about −30° C. to about 100° C., for example at the boil, and/or under an inert gas, for example under nitrogen. Preferred embodiments of this process are, in particular, the reaction of lithium compounds or halogenomagnesium compounds of the formula IV with carbon dioxide, a lower alkyl halogenoformate, for example a lower alkyl chloroformate or bromoformate, or a carbamyl halide, for example with carbamyl chloride or N,N-di-lower alkyl-carbamyl chlorides.

The starting materials of the formulae IV and V are known or, if they are novel, can be prepared by methods known per se.

The metal-organic compounds of the formula IV to be used as starting materials are advantageously prepared in situ by reacting a corresponding halogen compound, for example a chlorine, iodine or, in particular, bromine compound, preferably in an ether, for example in diethyl ether or tetrahydrofuran, with lithium or, in particular, magnesium, or reacting the corresponding compound which is unsubstituted in the 2-position in a conventional manner with a hydrocarbon-metal compound, such as butyl-lithium, butyl-magnesium bromide or phenyl-lithium. Other metal-organic compounds can be obtained from the halogeno-magnesium compounds, and in particular bromo-magnesium compounds, thus obtainable, by reaction with a corresponding metal halide, for example with cadmium chloride, copper chloride or zinc chloride. The halogen compounds to be used for this reaction can be prepared, for example, by reacting a corresponding $R_1$-X-1,2-phenylenediamine, which can be substituted on one amino group by a radical $R_2$ and is accessible, for example, from the corresponding halogenodinitrobenzene by reduction of the nitro groups, for example with hydrogen and Raney nickel, with a reactive derivative of carbonic acid, for example with a di-lower alkyl carbonate or with phosgene and halogenating the 2-hydroxy compound, first obtained, in a conventional manner, for example with phosphorus trichloride or phosphorus pentachloride or thionyl chloride. Compounds which are unsubstituted in the 2-position and correspond to the starting materials of the formula IV can also be prepared in an analogous manner, by reacting a corresponding 1,2-diaminohalogenobenzene, aminonitro- or $R_2$-aminonitrohalogenobenzene with formic acid or an ester thereof and, if appropriate, reducing the nitro group, whereupon cyclisation takes place.

The novel compounds in which $R_1$-X- is an aliphatic, cycloaliphatic, cycloaliphatic-aliphatic, araliphatic or heterocyclic-aliphatic radical can also be prepared by reducing the group $X_6$ in a corresponding compound of the formula

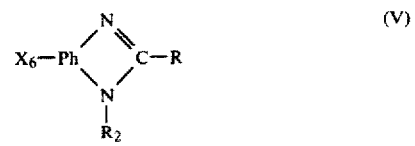

in which $X_6$ is a radical which is reducible to the group of the formula $R_1$-X, or in a salt thereof, to the desired group of the formula $R_1$-X- and, if desired, converting a compound of the formula I, thus obtainable, into another compound of the formula I and/or, if desired, converting a resulting salt into the free compound or into another salt and/or converting a free salt-forming compound into a salt.

Radicals which are reducible to the said groups of the formula $R_1$-X- are, for example, aliphatic, cycloaliphatic, araliphatic, cycloaliphatic-aliphatic or heterocyclic-aliphatic radicals which contain at least one double or triple bond in the aliphatic and/or cycloaliphatic moiety or are substituted by at least one radical $X_7$ which is replaceable by hydrogen, by reduction. Radicals of the said type containing at least one double or triple bond are, for example, corresponding alkenyl or alkynyl radicals, cycloalkenyl, cycloalkenylalkyl or cycloalkenylalkenyl radicals, aralkyl radicals or heteroarylalkenyl radicals. Radicals of the said type which are substituted by at least one radical $X_7$ which is replaceable by hydrogen by reduction, the radical $X_7$ being, for example, hydroxyl, oxo or halogen, such as chlorine, are, for example, $X_7$-alkyl radicals, $X_7$-cycloalkylalkyl or cycloalkyl-$X_7$-alkyl radicals, aryl-$X_7$-alkyl radicals or heteroaryl-$X_7$-radicals, preferably of the formula $R_1$-CH($X_7$)-, such as $R_1$-CH(OH)—.

The group $X_6$, which, as a group $X_6$ which contains hydroxyl $X_7$ and has, for example, the formula $R_1$-CH(OH)—, can also be formed in situ in the course of the oxidation reaction, for example from the corresponding group which contains oxo as a substituent and has, for example, the formula $R_1$-C(=O), or can be set free from one of its derivatives, such as an ester, for example a hydrogen halide acid ester or a lower alkanoic acid ester, is reduced in a conventional manner. The reducing agent is, for example, catalytically activated hydrogen, such as hydrogen in the presence of a hydrogenation catalyst, for example of a platinum, palladium or nickel catalyst, for example of palladium-on-charcoal. The reaction is advantageously carried out in the presence of a suitable solvent or diluent, such as ethanol, at normal temperature or, if necessary, with cooling or warming, for example in a temperature range from about 0° C. to about 80° C.

The compounds of the formula VI to be used as starting materials can be prepared, for example, by, in a manner known per se, acylating a corresponding chlorobenzene of the formula H-PhH-Cl by reaction with a compound which introduces the radical $X_6$, for example a compound of the formula $R_1$-COHal or $(R_1CO)_2O$, in the presence of aluminium trichloride, nitrating the compound of the formula $X_6$-PhH-Cl, thus obtainable, with nitric acid/sulphuric acid and reacting the chloronitro compound of the formula $X_6$-Ph(Cl)-$NO_2$, for example of the formula $R_1$-CO-Ph(Cl)-$NO_2$, thus obtainable, with ammonia or an amine of the formula $R_2NH_2$, reducing the compound of the formula $X_6$-Ph($NHR_2$)-$NO_2$ thus obtainable under mild conditions, for example with hydrogen in the presence of palladium-on-charcoal, advantageously in an inert solvent, such as ethanol, if appropriate in the presence of hydrogen chloride and under normal temperature and pressure conditions, and subjecting the compound $X_6$-Ph($NHR_2$)-$NH_2$, for example of the formula $R_1$-CH(OH)-Ph($NHR_2$)-$NH_2$, thus obtainable, to a condensation reaction with an acid of the formula R-COOH or a suitable functional derivative thereof, for example a lower alkyl ester thereof.

A compound of the formula I obtainable according to the invention can be converted to another compound of the formula I in a manner known per se.

Thus, in a compound of the formula I in which R is carboxyl the latter can be converted to an esterified carboxyl group by esterification methods known per se. Thus, for example, esterification can be carried out by treatment with a suitable diazo compound, such as a diazolower alkane, with a suitable N,N-di-lower alkyl-formamide acetal, for example N,N-dimethylformamide diethyl acetal or N,N-dimethylformamide methosulphate, or with an oxonium salt, such as with a tri-lower alkyloxonium tetrafluoborate or hexafluorophosphate, with a carbonate or pyrocarbonate, for example with diethyl (pyro)carbonate, or with an organic sulphite or phosphite, such as a di-lower alkyl sulphite or tri-lower alkyl phosphite, in the presence of a suitable acid agent, such as p-toluenesulphonic acid, or with an alcohol in the presence of a suitable condensing agent, such as a dehydrating agent, for example dicyclohexylcarbodiimide, or, in order to form a hydroxylower alkyl group, with an epoxy-lower alkane, for example ethylene oxide. Furthermore, it is possible to react a compound of the formula I in which a free carboxyl group R is in the form of a salt, for example in the form of an alkali metal salt, such as in the form of the sodium salt, with a reactive ester of an alcohol, for example the ester with a strong acid, such as a corresponding halide, for example chloride, bromide or iodide, or a sulphuric acid ester, or to react a compound of the formula I in which a free carboxyl group R is in the form of an anhydride, preferably in the form of a halogenocarbonyl group, for example the chlorocarbonyl group, which can be formed, for example, by treating a compound of the formula I in which R is carboxyl with a halogenating agent, for example thionyl chloride, with a metal alcoholate or an alcohol in the presence of an acid-binding base, and thus to obtain a compound of the formula I in which R is esterified carboxyl. Any substituents which may be present in an esterifying reagent can be in a functionally modified form and then be set free in a compound of the formula I in which R is, for example, substituted lower alkoxycarbonyl in which substituents are in a functionally modified form. Thus, for example, 2,3-epoxypropyl chloride can be used as the esterifying agent and a 2,3-epoxy-propoxy grouping R in the resulting ester can subsequently be hydrolysed to the desired 2,3-dihydroxypropoxy grouping.

In a compound of the formula I in which R is esterified carboxyl, for example including p-nitro- or 2,4-dinitro-phenoxy- or -benzyloxy-carbonyl, this can be converted to another esterified carboxyl group by transesterification, for example by treatment with an alcohol, if necessary in the presence of a suitable transesterification catalyst, such as a substituted or unsubstituted alkali metal alkanolate, for example a substituted or unsubstituted sodium or potassium alkanolate.

In a resulting compound of the formula I in which R is free carboxyl, carboxyl in the form of an anhydride or esterified carboxyl, this can also be converted to substituted or unsubstituted carbamyl in a manner known per se. Thus, it is possible to treat a compound of the formula I in which a carboxyl group R is in the form of an anhydride, especially in the form of a halogenocarbonyl group, for example a chlorocarbonyl group, or in an esterified form, with ammonia, hydroxylamine or a primary or secondary amine and thus to obtain compounds of the formula I in which R is substituted or unsubstituted carbamyl. Furthermore, the ammonium salt or an amine salt of a compound of the formula I in which R is carboxyl can be converted by dehydration with a suitable dehydrating agent, such as sulphuric acid, to a compound of the formula I in which R is substituted or unsubstituted carbamyl.

The said compounds in which R is carboxyl in the form of a halide can be prepared using compounds of the formula I in which R is carboxyl as the starting materials, by treatment with a thionyl halide, such as thionyl chloride. If $R_2$ is hydrogen, these compounds can be dimerised to compounds of the formula

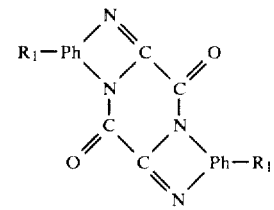

An intermediate of this type can, for example, be converted by treatment with a suitable alcoholate, such as an alkali metal alcoholate, for example a sodium or potassium alcoholate, or with an alcohol in the presence of a mineral acid, for example hydrogen chloride, or with ammonia, hydroxylamine or a primary or secondary amine, to a compound of the formula I in which R is esterified carboxyl or substituted or unsubstituted carbamyl.

In a compound of the formula I, an esterified carboxyl group or a substituted or unsubstituted carbamyl group R can be converted to the free carboxyl group in a conventional manner, for example by hydrolysis, usually in an alkaline medium, such as by treatment with water in the presence of an alkali metal hydroxide or alkaline earth metal hydroxide, for example sodium hydroxide.

In a compound of the formula I in which $R_2$ is hydrogen the latter can be replaced by an aliphatic radical, for example by treatment with a reactive ester of a corresponding alcohol, such as a halide, in the presence of a base, for example of an alkali metal alcoholate.

Furthermore, a free or esterified carboxyl group R or a carboxyl group R in the form of a halide or of a salt can be reduced to hydroxymethyl by reaction with a light metal borohydride or with hydrogen in the presence of a hydrogenation catalyst. A light metal hydride, such as a borane, for example diborane or the borane tetrahydrofuran complex, or a di-(light metal) hydride, such as lithium aluminium hydride, sodium borohydride or sodium cyanoborohydride is preferably used for the reduction of a free or esterified carboxyl group or of a carboxyl group in the form of an alkali metal salt, such as the sodium salt. Halogenocarbonyl groups, such as chlorocarbonyl, are preferably reduced with hydrogen in the presence of palladium, preferably on a support, such as barium sulphate, and if necessary in the presence of a sulphur-containing co-catalyst, for example of thiourea.

Furthermore, in a compound of the formula I in which R is hydroxymethyl, the latter can be converted to an etherified hydroxymethyl group in a conventional manner, for example by reaction with an etherifying agent. Etherifying agents are, for example, reactive esters of corresponding alcohols, for example the esters thereof with inorganic acids, such as hydrochloric acid, hydrobromic acid or hydriodic acid or sulphuric acid, or with organic sulphonic acids, for example with methanesulphonic acid, benzenesulphonic acid, p-bromobenzenesulphonic acid or p-toluenesulphonic acid, and also epoxides derived from corresponding 1,2-diols. The reaction with the said etherifying agents can be carried out in a conventional manner, for example in the presence of an alkali metal hydride or alkali metal alcoholate, for example of sodium hydride or sodium methanolate, or by using the compound to be etherified in the form of a salt, for example the sodium salt. Furthermore, in a compound of the formula I in which R is hydroxymethyl the latter can be esterified in a conventional manner and, for example, can be converted to an esterified hydroxymethyl group R by direct esterification with a corresponding carboxylic acid in the presence of a mineral acid, for example of hydrochloric acid or sulphuric acid, or by reaction with a reactive derivative, for example an anhydride, such as the anhydride or chloride, or an ester, such as a lower alkyl ester or the o-nitrophenyl or 2,4-dinitrophenyl ester, of the carboxylic acid, if necessary in the presence of an acid or, in particular, a basic condensing agent, for example in the presence of pyridine in the case of the reaction with an acid anhydride and, for example, in the presence of an alkali metal alcoholate, such as a sodium or potassium alcoholate, in the case of the reaction with an ester. The etherification or esterification of a hydroxymethyl group can, however, also be carried out by first converting this group to a halogenomethyl group in a conventional manner, for example using phosphorus tribromide or thionyl chloride, and then reacting the product with an alkali metal alcoholate, for example the sodium alcoholate, of the corresponding alcohol, or, respectively, with an alkali metal salt, for example the sodium salt, of the corresponding carboxylic acid.

Free or esterified hydroxymethyl groups R can also be oxidised to carboxyl groups and etherified hydroxymethyl groups can be oxidised to esterified carboxyl groups. The oxidation can be carried out in a manner known per se, for example by reaction with an oxidising heavy metal compound, preferably with an oxidising compound containing chromium-VI or manganese-VII, for example with chromium trioxide or especially potassium permanganate, when starting from a hydroxymethyl group, and also with a compound containing manganese-IV, such as manganese dioxide, when starting from etherified hydroxymethyl R. The reaction is preferably carried out in the presence of a suitable solvent or diluent, for example of acetone or pyridine, or of a mixture thereof, preferably an aqueous mixture thereof, if necessary with cooling or warming, for example in a temperature range from about 0° C. to about 80° C.

Resulting free salt-forming compounds of the formula I can be converted to salts in a manner known per se; acids, for example, can be converted to salts with a base or with a suitable salt of a carboxylic acid and bases can be converted to salts with a mineral acid, usually in the presence of a solvent or diluent.

Resulting salts can be converted to the free compounds in a manner known per se, for example by treatment with an acid reagent, such as a mineral acid.

The compounds, including their salts, can also be obtained in the form of their hydrates or can incorporate the solvent used for crystallisation.

Because of the close relationship between the novel compounds in the free form and in the form of their salts, what is stated in this specification in respect of the free compounds or the salts thereof also applies by analogy to the corresponding salts and free compounds.

The invention also relates to those embodiments of the process in which a compound obtainable as an intermediate at any process stage is used as the starting material and the missing process steps are carried out, or a starting material is formed under the reaction conditions or is used in the form of a derivative thereof, if desired in the form of a salt.

The starting materials used in the process of the present invention are preferably those which result in the compounds described initially as being particularly valuable. Novel starting materials and processes for their preparation likewise constitute a subject of the present invention.

The present invention also relates to pharmaceutical preparations which contain compounds of the formula I or pharmaceutically usable salts thereof. The pharmaceutical preparations according to the invention are those intended for enteral, such as oral, nasal or rectal, and also parenteral administration or topical application to warm-blooded animals and contain the pharmacological active ingredient on its own or together with a pharmaceutically usable carrier. The dosage of the active ingredient depends on the species of warm-blooded animal, the age and the individual condition and also on the mode of administration.

The novel pharmaceutical preparations contain, for example, up to about 95%, preferably from about 5% to about 90%, of the active ingredient. Pharmaceutical preparations according to the invention are, for example, those in the form of dosage units, such as sugar-coated tablets, tablets, capsules or suppositories, and ampoules and also inhalation preparations, and also pharmaceutical preparations which can be used topically and locally (for example for insufflation).

The pharmaceutical preparations of the present invention are prepared in a manner known per se, for example by means of conventional mixing, granulating, sugar-coating, dissolving or lyophilising methods. Thus, pharmaceutical preparations for oral administration can be obtained by combining the active ingredient with solid carriers, granulating a resulting mixture if desired and processing the mixture or granules, after the addition of suitable adjuncts if desired or necessary, to tablets or sugar-coated tablet cores.

Suitable carriers are in particular fillers, such as sugars, for example lactose, sucrose, mannitol or sorbitol, cellulose preparations and/or calcium phosphates, for example tricalcium phosphate or calcium hydrogen phosphate, and also binders, such as starch pastes using, for example, maize, corn, rice or potato starch, gelatin, tragacanth, methylcellulose and/or polyvinylpyrrolidone, and/or, if desired, disintegrators, such as the above starches, and also carboxymethylstarch cross-linked polyvinylpyrrolidone, agar or alginic acid or a salt thereof, such as sodium alginate. Adjuncts are in particular glidants and lubricants, for example silicic acid, talc, stearic acid or salts thereof, such as magnesium stearate or calcium stearate, and/or polyethylene glycol. Sugar-coated tablet cores are provided with suitable coatings which can be resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or sugar-coated tablet cores, for example to identify or characterise different doses of active ingredient.

Further pharmaceutical preparations for oral administration are dry-filled capsules made of gelatin and also soft sealed capsules made of gelatin and a plasticiser, such as glycerin or sorbitol. The dry-filled capsules can contain the active ingredient in the form of granules, for example in admixture with fillers, such as lactose, binders, such as starches, and/or lubricants, such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers can also be added.

Pharmaceutical preparations which can be administered rectally are, for example, suppositories, which consist of a combination of the active ingredient with a suppository base. Examples of suitable suppository bases are natural or synthetic triglycerides, paraffin hydrocarbons, polyethylene glycols or higher alkanols. Gelatin rectal capsules, which contain a combination of the active ingredient with a base, can also be used; base materials are, for example, liquid triglycerides, polyethylene glycols or paraffin hydrocarbons.

Suitable preparations for parenteral administration are, in particular, aqueous solutions of an active ingredient in a water-soluble form, for example of a water-soluble salt, and also suspensions of the active ingredient, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions, which contain substances which increase the viscosity, for example sodium carboxymethylcellulose, sorbitol and/or dextran, and can also contain stabilisers.

Inhalation preparations for the treatment of the respiratory passages by nasal or buccal administration are, for example, aerosols or sprays which can disperse the pharmacological active ingredient in the form of a powder or in the form of drops of a solution or suspension. Preparations which have powder-dispersing properties usually contain, in addition to the active ingredient, a liquid propellant gas which has a boiling point below room temperature and also, if desired, carriers, such as liquid or solid non-ionic or anionic surfactants and/or solid diluents. Preparations in which the pharmacological active ingredient is in solution contain, in addition to this active ingredient, a suitable propellant and also, if necessary, an additional solvent and/or a stabiliser. In place of the propellant gas, it is also possible to use compressed air and this can be produced as required by means of a suitable compression and pressure release device.

Pharmaceutical preparations for topical and local use are, for example, lotions and creams which contain a liquid or semi-solid oil-in-water or water-in-oil emulsion, and ointments (such preparations preferably containing a preservative) for the treatment of the skin, eyedrops which contain the active ingredient in aqueous or oily solution and eye ointments, which are preferably prepared in a sterile form, for the treatment of the eyes, powders, aerosols and sprays (similar to those described above for the treatment of the respiratory passages) and also coarse powders, which are administered through the nostrils by rapid inhalation, and nose drops, which contain the active ingredient in aqueous or oily solution, for the treatment of the nose, or lozenges, which contain the active ingredient in a composition generally consisting of sugar and gum arabic or tragacanth, to which flavourings can be added, as well as pastilles, which contain the active ingredient in an inert composition, for example consisting of gelatin and glycerin or sugar and gum arabic, for the local treatment of the mouth.

The invention also relates to the use of the novel compounds of the formula I, or salts thereof, as pharmacologically active compounds and especially as antiallergic agents, preferably in the form of pharmaceutical preparations. The daily dose which is administered to a warm-blooded animal weighing about 70 kg is from about 2 mg to about 7,000 mg depending on the mode of administration.

The following examples illustrate the present invention without in any way restricting the scope thereof. Temperatures are in degrees centigrade.

EXAMPLE 1

20.8 g of ethoxyacetic acid are added to 23 g of crude 4-butyl-1,2-phenylene-diamine and the mixture is heated at 130° for 90 minutes. It is allowed to cool and is taken up in ethyl acetate, washed with sodium bicarbonate solution and then three times with water, dried over sodium sulphate and filtered and the filtrate is evaporated to dryness under reduced pressure. The residue is chromatographed on 600 g of silica gel using chloroform as the solvent. After a small initial fraction, 2-ethoxymethyl-5-butyl-benzimidazole is obtained in the main fraction.

The starting material can be prepared as follows:

A mixture of 40 ml of sulphuric acid and 21 ml of fuming nitric acid is added in the course of 5 minutes, at −20° to −15°, to a solution of 18.3 g of 4-chloro-butyrophenone in 100 ml of sulphuric acid at −20° and all constituents go into solution. The solution is stirred for a further 45 minutes at −15° to −10° and is poured onto 1,000 g of ice. The mixture is filtered with suction and the material on the filter is washed with water and taken up in chloroform, the chloroform solution is washed with saturated sodium bicarbonate solution and twice with water, dried over sodium sulphate and filtered and the filtrate is evaporated to dryness. The evaporation residue is digested with 25 ml of methanol. This yields 4-chloro-3-nitro-butyrophenone with a melting point of 52°-54°.

50 g of ammonia are injected into an autoclave containing a solution of 22.8 g of 4-chloro-3-nitrobutyrophenone in 300 ml of ethanol. The mixture is warmed at 100° for 10 hours and after cooling to room temperature is evaporated to dryness under reduced pressure, the evaporation residue is warmed with 200 ml of 2 N hydrochloric acid for 1 hour at 80°-90°, the mixture is cooled to 15° by adding ice and is filtered with suction and the material on the filter is washed with water. The material on the suction filter is taken up in 1,000 ml of methylene chloride, the solution is dried over sodium sulphate and concentrated, petroleum ether (boiling range 60°-80°) is added and all of the methylene chloride is evaporated off. 4-Amino-3-nitro-butyrophenone, which has precipitated as a crystalline product, is filtered off with suction and dried in vacuo. It melts at 128°-129°.

19.9 g of 4-amino-3-nitro-butyrophenone are dissolved in about 300 ml of ethanol and 15 ml of 12.8% ethanolic hydrochloric acid and, after adding 5% palladium-on-charcoal (2 g), hydrogenated at about 30°-35° until 11.2 l of hydrogen have been taken up. The catalyst is filtered off and the filtrate is evaporated under reduced pressure. The residue is taken up in ether and the solution is dried over sodium sulphate and evaporated. This yields 4-butyl-1,2-phenylenediamine which can be further reacted without further purification.

EXAMPLE 2

4.65 g of 2-ethoxymethyl-5-butyl-benzimidazole are dissolved in 100 ml of acetone and 5 ml of water, 5 g of potassium permanganate are added and the mixture is refluxed for 6 hours, 1 g portions of potassium permanganate (a total of 10 g) being added at approximately half hour intervals. The mixture is then filtered hot and the filtrate is evaporated under reduced pressure. The residue is taken up in ethyl acetate, ice is added and the mixture is extracted by shaking with slightly acidified sodium bisulphite solution. The aqueous phase is separated off and twice extracted by shaking with ethyl acetate. The organic phases are combined, washed twice with water, dried over sodium sulphate and evaporated. This yields ethyl 5-butyl-benzimidazole-2-carboxylate in the form of a yellowish oil, which after standing for some time crystallises spontaneously (melting point 129°-130°).

EXAMPLE 3

25 g of 5-butyl-6-methyl-2-methylaminoaniline bishydrochloride are dissolved in 150 ml of 2 N hydrochloric acid, 15.6 g of ethoxyacetic acid are added and the mixture is refluxed for 5 hours. It is allowed to cool, ice is added and the mixture is rendered alkaline with concentrated sodium hydroxide solution and extracted three times with ethyl acetate. The extract is washed twice with water, dried over sodium sulphate and evaporated to dryness under reduced pressure. This yields 2-ethoxymethyl-5-butyl-1,6-dimethyl-benzimidazole.

The starting material can be obtained as follows:

266 g of butyric acid chloride are added in the course of one hour to a yellow suspension of 900 ml of 3-chloro-toluene and 367.5 g of aluminuim chloride (finely powdered). Hydrogen chloride gas is evolved during the dropwise addition; the reaction is exothermic (the temperature is allowed to rise to 70°) and the aluminuim chloride dissolves. After the addition of the butyric acid chloride is complete, the reaction mixture is kept at 70° until the evolution of gas has ceased (about 45 minutes) and is then cooled to 50° and poured onto 2,500 g of ice.

Two identical batches are combined and extracted with ethyl acetate; the organic extract is washed twice with 2 N hydrochloric acid, once with a saturated aqueous solution of sodium chloride, twice with a 2 N aqueous solution of sodium carbonate and once with a saturated aqueous solution of sodium chloride, dried and evaporated. The brown oily residue, thus obtainable, is distilled; a mixture of 4-chloro-2-methyl-butyrophenone and 2-chloro-4-methyl-butyrophenone is obtained at 160°-164°/14 mm Hg.

285.5 g of the mixture of 4-chloro-2-methyl-butyrophenone and 2-chloro-4-methyl-butyrophenone are added dropwise in the course of 10 minutes to concentrated sulphuric acid (1,275 ml), which has been cooled to −20° to −25° by means of a carbon dioxide/chloroform mixture, with good stirring. The resulting solution is treated at −20° to −25° in the course of 30 minutes with a mixture of 240 ml of concentrated sulphuric acid and 75 ml of 100% nitric acid (d:1.52) and then stirred for a further 15 minutes, during which time the temperature is allowed to rise to −15°. The mixture is poured into 8,000 ml of ice-water; the oil which has precipitated is extracted with chloroform. The organic extract is washed once with an aqueous solution of sodium bicarbonate and once with water, dried over sodium sulphate and evaporated. The residue is dissolved in twice the amount of hot methanol and the solution is left to stand for 16 hours. The crystalline precipitate is filtered off, washed with cold water and dried at 100 mm Hg and room temperature for 18 hours. This yields 4-chloro-2-methyl-5-nitro-butyrophenone, which melts at 71°-72°.

A mixture of 24.1 g of 4-chloro-2-methyl-5-nitro-butyrophenone and 250 ml of a 33% solution of methylamine in ethanol is left to stand at room temperature; the crystalline starting material dissolves slowly and a yellow coloration develops. The reaction is slightly exothermic; the reaction mixture is therefore cooled with a waterbath in order to prevent too large an amount of methylamine from escaping. After 20 minutes, dissolution is complete and a precipitate then starts to separate out. The mixture is left to stand for 16 hours at room temperature and is then evaporated to dryness under reduced pressure. Diethyl ether (about 1,000 ml), ice and sodium carbonate are added to the residue, the mixture is shaken thoroughly and the organic layer is separated off. This is washed twice with water and the aqueous solution is back-washed with diethyl ether. The combined organic solutions are dried over sodium sulphate, filtered and evaporated to a volume of about 300 ml, then diluted with 100 ml of petroleum ether and cooled. Yellow crystalline 2-methyl-4-methylamino-5-nitro-butyrophenone precipitates out and is filtered off, washed with petroleum ether and dried in air; melting point 107°–108°.

The conversion of 4-chloro-2-methyl-5-nitro-butyrophenone to 4-amino-2-methyl-5-methylamino-butyrophenone can also be carried out in the following manner and it is also possible to use a crude mixture of isomers as the starting material.

241 g of crude chloro-methyl-nitrobutyrophenone (containing about 75% of 4-chloro-2-methyl-5-nitro-butyrophenone) are suspended in 1,200 ml of ethanol, and 1,200 ml of 33% methylamine solution are added to the suspension, whereupon the solid dissolves, an exothermic reaction taking place. The solution is left to stand for 2 days and is evaporated to dryness under reduced pressure, 600 ml of 2 N hydrochloric acid are added to the residue and the mixture is warmed at 80°–90° for 1 hour. The mixture is cooled to about 15° by adding ice and the crystalline precipitate is filtered off with suction, washed with water and taken up in methylene chloride, the methylene chloride solution is dried over sodium sulphate, the methylene chloride is evaporated off under reduced pressure, finally with the addition of cyclohexane and petroleum ether (boiling range 60°–80°), the residual mixture is cooled and 2-methyl-4-methylamino-5-nitrobutyrophenone with a melting point 105°–107° is filtered off with suction.

23.6 g of 2-methyl-4-methylamino-5-nitro-butyrophenone are dissolved in 240 ml of ethanol and 57 ml of 12.8% ethanolic hydrochloric acid, 5% palladium-on-charcoal (7.4 g) is added and the mixture is hydrogenated at 30°–35° until 11.6 liters of hydrogen have been taken up. The catalyst is filtered off, the filtrate is evaporated to dryness under reduced pressure, the evaporation residue is suspended in toluene, the water is distilled off azeotropically and the crystals of 4-butyl-6-methyl-2-methylamino-aniline bis-hydrochloride with a melting point above 160° are filtered off.

EXAMPLE 4

In a manner analogous to that described in Example 2, 27.0 g of crude 2-ethoxymethyl-5-butyl-1,6-dimethyl-benzimidazole are oxidised with 50 g of potassium permanganate to ethyl 5-butyl-1,6-dimethyl-benzimidazole-2-carboxylate with a melting point of 56°–57°.

EXAMPLE 5

45 g of crude 4-butyl-2-methylamino-aniline bis-hydrochloride are dissolved in 200 ml of 2 N hydrochloric acid, 23.4 g of ethoxyacetic acid are added and the mixture is refluxed for 2 hours. It is allowed to cool, concentrated sodium hydroxide solution is added until the mixture gives a distinct alkaline reaction and the resulting mixture is extracted three times with ethyl acetate. The extracts are combined, washed twice with water, dried over sodium sulphate and evaporated under reduced pressure. The evaporation residue is recrystallised from a little petroleum ether. This yields 2-ethoxymethyl-5-butyl-1-methyl-benzimidazole with a melting point of 55°–58°.

The starting material can be prepared in a manner analogous to that described in Example 3, using chlorobenzene as the starting material and via 4-chlorobutyrophenone and 4-chloro-3-nitrobutyrophenone.

EXAMPLE 6

8.9 g of 2-ethoxymethyl-5-butyl-1-methyl-benzimidazole are dissolved in 180 ml of acetone and 9 ml of water, 10 g of potassium permanganate are added and the mixture is stirred for 2 hours at room temperature. It is then refluxed for about 7 hours, 2 g portions of potassium permanganate (a total of 22 g) being added at approximately half hour intervals. The mixture is allowed to cool and is filtered through diatomaceous earth, the filtrate is evaporated to dryness under reduced pressure and the evaporation residue is taken up in ethyl acetate. The solution is extracted by shaking with sodium bisulphite solution, washed twice with water, dried over sodium sulphate and evaporated under reduced pressure. The evaporation residue is chromatographed on silica gel using a mixture of equal parts of chloroform, petroleum ether and ethyl acetate as the solvent. This yields ethyl 5-butyl-1-methyl-benzimidazole-2-carboxylate with a melting point of 49°–50°.

EXAMPLE 7

7 g of ethyl 5-butyryl-6-methyl-benzimidazole-2-carboxylate are dissolved in 140 ml of ethanol and, after adding 5% palladium-on-charcoal (3.5 g), hydrogenated at 20°–50°. The catalyst is filtered off, the filtrate is evaporated to dryness and the evaporation residue is chromatographed on silica gel using methylene chloride/ethyl acetate (1:1) as the solvent. This yields ethyl 5-butyl-6-methyl-benzimidazole-2-carboxylate with a melting point of 123°–125°.

The starting material can be prepared as follows:

22.2 g of 4-amino-2-methyl-5-nitro-butyrophenone are dissolved in 230 ml of methanol, 2 g of Raney nickel are added and the mixture is hydrogenated at 15°–25° under normal pressure until 4.9 liters of hydrogen have been taken up. 20.8 g of ethoxyacetic acid are added under nitrogen, the catalyst is filtered off, the filtrate is evaporated under reduced pressure and the residue is heated at 130° for 3 hours. After cooling, the residue is dissolved in 200 ml of 2 N hydrochloric acid, the solution is washed twice with ethyl acetate, rendered alkaline in the cold with sodium carbonate and extracted twice with ethyl acetate, the extracts are dried over sodium sulphate and evaporated and the evaporation residue is chromatographed on 300 g of silica gel. A first fraction is initially eluted with 1,200 ml of chloroform and 2-ethoxymethyl-5-butyryl-6-methyl-benzimidazole is then eluted with 1,200 ml of chloroform/ethanol (24:1).

15 g of potassium permanganate are added to a solution, which has been cooled to 10°, of 18.9 g of 2-ethoxymethyl-5-butyryl-6-methyl-benzimidazole in 380 ml of acetone, 9.5 ml of pyridine and 5.7 ml of water, with stirring. The mixture is stirred for a further 1 hour with ice-cooling and for 40 hours at room temperature and filtered, the filtrate is evaporated to dryness under reduced pressure, the residue is taken up in ethyl acetate and the solution is washed successively with sodium bicarbonate solution buffered to pH 6 and twice with water, dried over sodium sulphate and evaporated under reduced pressure. The evaporation residue is then taken up in 30 ml of warm ethyl acetate, the solution is left to stand overnight and crystalline ethyl 5-butyryl-6-methyl-benzimidazole-2-carboxylate with a melting point of 137°–139° is filtered off with suction. Further product with a melting point of 129°–132° can be obtained from the mother liquor. Recrystallisation from ethyl acetate/methylene chloride raises the melting point to 146°–147°.

EXAMPLE 8

In a manner analogous to that described in Example 1, the reaction of 25 g of 5-butyl-6-methyl-2-methylamino-aniline bis-hydrochloride with 11.5 g of glycollic acid yields 2-hydroxymethyl-5-butyl-1,6-dimethyl-benzimidazole in the form of a viscous oil.

EXAMPLE 9

In a manner analogous to that described in Example 2, the oxidation of 8.5 g of 2-hydroxymethyl-5-butyl-1,6-dimethyl-benzimidazole with 24 g of potassium permanganate in 200 ml of 95% aqueous acetone yields 5-butyl-1,6-dimethyl-benzimidazole-2-carboxylic acid.

EXAMPLE 10

A 2% aqueous solution, which is suitable for inhalation, of the sodium salt of 5(6)-methyl-benzimidazole-2-carboxylic acid can be prepared as follows:

| Composition: (for 100 ml) | |
|---|---|
| sodium salt of 5(6)-methyl-benzimidazole-2-carboxylic acid | 2,000 g |
| disodium salt of ethylenediamine-tetraacetic acid (stabiliser) | 0.010 g |
| benzalkonium chloride (preservative) | 0.010 g |
| distilled water | to make up to 100 ml |

The sodium salt of 5(6)-methyl-benzimidazole-2-carboxylic acid is dissolved in freshly distilled water, and the disodium salt of ethylenediamine-tetraacetic acid and the benzalkonium chloride (a mixture of alkyl-dimethyl-benzyl-ammonium chloridesin which alkyl contains from 8 to 18 carbon atoms) are added to the solution. After all of the components have completely dissolved, the resulting solution is made up to a volume of 100 ml with water and filled into containers and the latter are sealed gas-tight.

2% aqueous inhalation solutions of the sodium salt of 5,6-dimethyl-benzimidazole-2-carboxylic acid or 5-butyl-1,6-dimethyl-benzimidazole-2-carboxylic acid can be prepared analogously.

EXAMPLE 11

Capsules which are suitable for insufflation and contain 0.025 g of ethyl 5-butyl-1,6-dimethyl-benzimidazole-2-carboxylate can be prepared as follows:

| Composition: (for 1,000 capsules) | |
|---|---|
| ethyl 5-butyl-1,6-dimethyl-benzimidazole-2-carboxylate | 25.00 g |
| ground lactose | 25.00 g |

The ethyl 5-butyl-1,6-dimethyl-benzimidazole-2-carboxylate and the lactose (very finely ground) are mixed well with one another. The resulting powder is then sieved and filled in portions of 0.05 g into gelatin capsules.

Insufflation capsules each containing 0.025 g of 2-ethoxymethyl-5-butyl-1-methyl-benzimidazole, 2-ethoxymethyl-5-butyl-1,6-dimethyl-benzimidazole, 2-ethoxymethyl-5-butyl-benzimidazole, ethyl 5-butyl-benzimidazole-2-carboxylate, ethyl 5-butyl-1-methyl-benzimidazole-2-carboxylate or ethyl 5-butyl-6-methyl-benzimidazole-2-carboxylate can also be prepared in an analogous manner.

EXAMPLE 12

Tablets containing 100 mg of ethyl butyl-1,6-dimethyl-benzimidazole-2-carboxylate (active ingredient) can be prepared, for example, in the following composition:

| Composition | Per tablet |
|---|---|
| ethyl 5-butyl-1,6-dimethyl-benzimidazole-2-carboxylate | 100 mg |
| lactose | 50 mg |
| corn starch | 73 mg |
| colloidal silica | 13 mg |
| talc | 12 mg |
| magnesium stearate | 2 mg |
| | 250 mg |

Preparation

The active ingredient is mixed with the lactose, a portion of the corn starch and with colloidal silica and the mixture is forced through a sieve. A further portion of the corn starch is mixed to a paste with 5 times the amount of water on a waterbath and the powder mixture is kneaded with this paste until a slightly plastic mass has formed. The mass is forced through a sieve of about 3 mm mesh width and dried and the dry granules are again forced through a sieve. The remainder of the corn starch, the talc and the magnesium stearate are then mixed in. The resulting mixture is compressed to tablets weighing 250 mg, with a breaking notch or notches.

Tablets each containing 100 mg of one of the compounds listed below can also be prepared in an analogous manner and these compounds can also be used in the form of pharmaceutically usable salts, for example, in the case of carboxylic acids, salts with a base, such as sodium salts: ethyl 5-butyl-6-methyl-benzimidazole-2-carboxylate, ethyl 5(6)-butyl-benzimidazole-2-carboxylate, 2-ethoxymethyl-5-butyl-1-methyl-benzimidazole, 2-ethoxymethyl-5-butyl-1,6-dimethyl-benzimidazole, 2-ethoxymethyl-5-butyl-benzimidazole and ethyl 5-butyl-1-methyl-benzimidazole-2-carboxylate.

EXAMPLE 13

In a manner analogous to that described in Examples 11 and 12, corresponding pharmaceutical preparations can be prepared using 2-hydroxymethyl-5-butyl-1,6-dimethyl-benzimidazole, 5(6)-methyl-benzimidazole-2-carboxylic acid, 5,6-dimethyl-benzimidazole-2-carboxylic acid, 5-butyl-1,6-dimethyl-benzimidazole-2-carboxylic acid, 2-hydroxymethyl-5(6)-methyl-benzimidazole or 5,6-dimethyl-2-hydroxymethyl-benzimidazole, if desired in the form of a salt, for example in the form of the sodium salt, as the active ingredient.

What is claimed is:

1. A benzimidazole-2-derivative of the formula

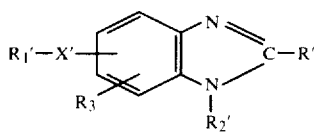

(Ia)

Ia, in which R' is carboxyl, hydroxymethyl or lower alkoxycarbonyl having a total of not more than 5 carbon atoms, $R_1'$-X' is lower alkyl of 4 carbon atoms and $R_2'$ is lower alkyl having not more than 4 carbon atoms and $R_3$ is hydrogen or lower alkyl having not more than 4 carbon atoms, or a pharmaceutically usable salt of said compound with salt-forming properties.

2. The compound as claimed in claim 1 being 5-butyl-1,6-dimethyl-benzimidazole-2-carboxylic acid or a pharmaceutically acceptable salt thereof.

3. The compound 5-butyl-2-ethoxymethyl-1,6-dimethyl-benzimidazole or a pharmaceutically acceptable salt thereof.

4. The compound as claimed in claim 1 being 5-butyl-2-hydroxymethyl-1,6-dimethyl-benzimidazole or a pharmaceutically acceptable salt thereof.

5. The compound as claimed in claim 1 being ethyl 5-butyl-1,6-dimethyl-benzimidazole-2-carboxylate or a pharmaceutically acceptable salt thereof.

* * * * *